(12) United States Patent
Martin et al.

(10) Patent No.: US 7,025,932 B2
(45) Date of Patent: Apr. 11, 2006

(54) CONTROL OF GASEOUS STERILIZATION

(75) Inventors: Anthony Martin, Andover (GB); David Watling, Dorking (GB)

(73) Assignee: Bioquell UK Limited, Hampshire (GB)

( * ) Notice: Subject to any disclaimer, the term of this patent is extended or adjusted under 35 U.S.C. 154(b) by 595 days.

(21) Appl. No.: 10/221,457

(22) PCT Filed: Mar. 21, 2001

(86) PCT No.: PCT/GB01/01254

§ 371 (c)(1),
(2), (4) Date: Sep. 11, 2002

(87) PCT Pub. No.: WO01/70282

PCT Pub. Date: Sep. 27, 2001

(65) Prior Publication Data

US 2003/0031589 A1    Feb. 13, 2003

(30) Foreign Application Priority Data

Mar. 21, 2000 (GB) .................................. 0006824

(51) Int. Cl.
*A61L 2/20* (2006.01)
(52) U.S. Cl. .............................. 422/3; 422/28; 422/32; 422/108
(58) Field of Classification Search ................ 422/28, 422/186, 3, 32, 108, 298, 299
See application file for complete search history.

(56) References Cited

U.S. PATENT DOCUMENTS

| 4,898,713 A | 2/1990 | Picard | |
| 4,956,145 A * | 9/1990 | Cummings et al. | 422/28 |

FOREIGN PATENT DOCUMENTS

| EP | 0 486 923 A1 | 5/1992 |
| EP | 0 486 623 B1 | 1/1997 |
| EP | 0 774 263 A | 5/1997 |
| GB | 2 354 443 A1 | 3/2001 |
| GB | 2 360 505 A | 9/2001 |
| WO | WO 97/47331 | 12/1997 |

OTHER PUBLICATIONS

Portner et al., *Sporicidal Effect of Peracetic Acid Vapor*, Applied Microbiology, vol. 16, No. 11, Nov. 1968, pp. 1782-1785.

Marcos-Martin et al, *Sterilization by Vapour Condensation*, Pharmaceutical Technology Europe, vol. 18, No. 2, Feb. 1999 (24-32).

Scatchard et al., *Vapor-Liquid Euquilibrium. VIII. Hydrogen Peroxide-Water Mixtures*, Journal of the American Chemical Society, vol. 74, No. 15, Aug. 6, 1952, pp. 3715-3720.

Swartling et al., *The Sterilizing Effect Against Bacillus subtilis Spores of Hydrogen Peroxide at Different Temperatures and Concentrations*, J. Dairy Res. vol. 35, 1968, pp. 423-428.

* cited by examiner

Primary Examiner—Krisanne Jastrzab
Assistant Examiner—Sean E. Conley
(74) Attorney, Agent, or Firm—Workman Nydegger

(57) ABSTRACT

A method of sterilizing a sealable enclosure includes initially adjusting the relative humidity in the enclosure to a level substantially below ambient, circulating a carrier gas to the enclosure at a temperature raised above ambient and supplying a sterilant vapor or vapors to the circulating carrier gas sufficient to saturate substantially the gas. On cooling in the enclosure, a condensate of the sterilant vapor is formed on surfaces in the enclosure, which is measured whilst continuing to circulate the gas/vapor until a required amount of condensate has been formed on a the surface. Supply of sterilant vapor to the gas is terminated whilst circulating the saturated gas/vapor continues to maintain the condensate on the enclosure surfaces for a predetermined period of time. Finally the sterilant vapor is extracted from the chamber.

12 Claims, 1 Drawing Sheet

CONTROL OF GASEOUS STERILIZATION

BACKGROUND OF THE INVENTION

1. Field of the Invention

The present invention relates to the method of controlling a gaseous surface sterilisation when the sterilisation effect is caused by condensation of the gas onto the surfaces.

2. Present State of the Art and Summary of the Invention

EP-A-0774263 discloses a method and apparatus for hydrogen peroxide vapour sterilisation. To sterilise a chamber, gas is circulated through the chamber and through a dehumidifier connected to the chamber. The humidity of the gas is monitored and, when the humidity is sufficiently low, hydrogen peroxide is introduced into the circulating gas until a suitable circulation of hydrogen peroxide in the gas has been reached. That level or greater of hydrogen peroxide is maintained for a suitable time, possibly adding additional hydrogen peroxide to the gas to maintain the level. After that time, the hydrogen peroxide is removed from the gas, for example by passing it over a metal catalyst which separates the hydrogen peroxide into water and oxygen. To measure the level of hydrogen peroxide in the gas, the gas containing the hydrogen peroxide may be diluted by a known ratio before passing through a sensor.

U.S. Pat. No. 4,898,713 discloses a process for sterilising an enclosure and an installation for performing the process in an enclosure equipped with a ventilation and filtration circuit. The enclosure is isolated and the internal relative humidity level is lowered by means of an assembly incorporating a drying cartridge. The sterilising agent is then introduced through a closed circuit until a relative humidity level close to the dew point is obtained. The sterilising agent is kept in the enclosure for a given contact time, before scavenging the agent by means of the ventilation and filtration circuit.

There are very many situations in the Pharmaceutical and Health Care industries when it is required to achieve surface sterilisation of both the walls of the chamber and the contents of that Chamber. Such situations would be when it is required to aseptically fill vials or other containers with a pharmaceutical product that cannot be terminally sterilised, or the decontamination of the outer wrapping of a bag containing a previously sterilised product, or to surface sterilise a medical device or instrument.

Such surface sterilisations are most commonly performed using gaseous techniques, as it is then possible to ensure that the gas reaches all parts of the surface. Most if not all of such gaseous surface sterilisation process are dependent upon the level of water vapour present as well as the concentration of the active gas. Dorothy M Portner et al (Reference I identified later) showed that Peracetic vapour was effective at an RH of 80% and ineffective at an RH of 20%. It was also reported by Lack (Reference II identified later) that formalin vapour is more effective at high relative humidity and similar claims have also been made for ozone and ethylene oxide.

Hydrogen peroxide gas generated from an aqueous solution, generally 30% w/w, has become the preferred gaseous sterilant in the pharmaceutical industry. The reasons for this choice is that it is sporicidal, fast, leave no residues and is non-persistent. The general understanding as taught in patent EP 0486623 BI has been that it is a dry gas process, and that condensation of the vapour is to be avoided.

Watling et al (Reference III identified later) has shown that rapid surface sterilisation is best achieved by promoting a fine layer of micro-condensation onto the surfaces to be sterilised. M. A. Marcos (4) has stated that condensation cannot be avoided in gaseous hydrogen peroxide sterilisation when operated as taught in patent EP 0486 923 BI.

The conventional measurements that are taken to ensure surface sterilisation are gas concentration, temperature, humidity and time. Attempts have been made to measure the gas concentration and water vapour content of the gas mixture but the results are generally suspect. We believe that this is primarily because the gas and water are generated at high temperature about 100° C., and then allowed to cool as they pass through the chamber where sterilisation is to take place. During this cooling process the vapours become saturated and droplet formation is inevitable. The instrumentation is therefore subjected to wet gas and unless special provision is made is unlikely to be able to measure the gaseous phase concentrations. Saturated vapour pressures of mixtures of hydrogen peroxide and water may be calculated from the activity coefficients given by Scatchard et al (5). The calculated saturated concentrations of water and hydrogen peroxide at room temperature are much lower than the concentration normally delivered to a chamber that is to be sterilised, and hence surface condensation will be unavoidable.

It has also been repeated by Swartling et al (6) that aqueous solutions of hydrogen peroxide are sporicidal and the 'D' values depend on concentration and temperature. If condensation is the primary cause of the sterilisation affect then the process should be treated as a wet process with similar results as those found by Swartling for aqueous solutions.

From our own experimental work we have shown that raising the temperature of the chamber to be sterilised will reduce the 'D' value, providing the time is taken from the onset of condensation, and reducing the temperature will have the reverse effect. The changes in 'D' value with temperature are very similar to those reported by Swartling.

From the above it may be seen that it is not gas concentration that should be controlled during most gaseous sterilisation processes. Whilst all the arguments are based on experimental work with hydrogen peroxide gas it would seem logical that a similar argument would also apply to those gases where water vapour is an essential part of the process.

This invention provides a method of sterilising a sealable enclosure comprising the steps of initially adjusting the relative humidity in the enclosure to a level substantially below ambient, circulating a carrier gas to the enclosure at a temperature raised above ambient, supplying a sterilant vapour or vapours to the circulating carrier gas sufficient to saturate substantially the gas whereby, on cooling in the enclosure, a condensate of the sterilant vapour is formed on surfaces in the enclosure, distributing the gas/vapour throughout the enclosure to ensure that a condensate of the sterilant vapour is formed on all surfaces of the enclosure, measuring the amount of condensate formed on a surface of the enclosure and continuing to circulate the gas/vapour until a required amount of condensate has been formed on said surface, and terminating supply of sterilant vapour to the gas whilst continuing to circulate the saturated gas/vapour to maintain the condensate on the enclosure surfaces for a predetermined period of time and finally extracting the sterilant vapour from the chamber.

Thus the gaseous Surface Sterilisation is a three-stage process. The first stage is to condition the chamber, and hence the surfaces inside the chamber, to a pre-determined humidity. This ensures that any organisms on the surface are dry and hence will form nuclei for condensation.

The second stage is to introduce the active gas and water vapour into the chamber to form a layer of condensation on the surfaces. This layer of condensation should be maintained for a sufficient period of time to achieve the required level of microbiological deactivation.

The final stage is the removal to a safe level of the active gas from the chamber.

The control of each phase of the sterilisation cycle may be achieved by the correct use of appropriate instrumentation and timers.

The first phase is dehumidification and is required to ensure that all of the surfaces inside the chamber to be sterilised have reached a stable condition with the air inside the chamber at the correct relative humidity. It has been found from experimental work that the fastest sterilisation cycles are achieved if the relative humidity is brought to 40% during the dehumidification stage. Higher relative humidity means that the microorganisms are not dry and any condensation is diluted by the water already surrounding the target. At lower relative humidity this gassing phase is extended because a larger quantity of sterilant is required to achieve condensation. It has also been found that with some chambers it may be necessary to hold the relative humidity at the 40% level in order to allow the surfaces to come to an equilibrium state.

The gassing stage of the sterilisation process is in three parts, the first to raise the concentration of the gas to the level at which condensation occurs. Once this has been achieved gassing should continue until the correct level of condensation has been provided. The process of deactivation of microorganisms is time dependent and it is therefore necessary to maintain the required level of condensation for a period of time. The length of time will depend on the type of microorganism to be killed and the temperature.

The deactivation time will normally be established for any particular microorganism presented in a defined fashion. Once this time is known at one temperature, then from the work of Swartling (6) a function may be generated to set an effective deactivation time at any other temperature. During this deactivation period of the gassing phase it is essential that the level of condensation is maintained. Evaporation may occur from the surfaces because of an increase in temperature or because fresh clean air is introduced into the system to make up for leakages. It is, therefore, essential that the output from the condensation monitor is linked to the gas generator so that the required level of condensation is maintained.

At the end of the gassing phase, including the time for deactivation, it is necessary to remove the active gas from the chamber. This may be done either by circulating the gas through a deactivation system to remove the active gas or by replacing the air and gas in the chamber with fresh clean air from an external source. It is, of course, possible to use a combination of these methods. The important factor is to reduce the active gas concentration to a safe level, and for hydrogen peroxide this is generally accepted to be 1 ppm. A gas sensor is required that will accurately measure low concentrations of the active gas so that access may be gained to the chamber at the earliest possible time.

Whilst the primary concern is always to be assured that a gassing sterilisation cycle has been effective, it is also important that this is achieved in the shortest possible time.

Generally the longest phase of any gaseous sterilisation cycle is the aeration phase, because of the time it takes for the gas to desorb from the surfaces. It is therefore important to ensure that sterilisation is achieved in the shortest possible time since absorption of the active gas will increase with time and the greater the amount of gas absorbed the longer it will take to achieve complete aeration.

The secondary benefit of accurately controlling the sterilisation using the critical parameters of condensation is time.

Since the critical parameter of condensation is being controlled with the associated time temperature functions then the sterility is assured parametrically, and since parametric control is used then it follows that the gassing phase may be optimized giving the shortest exposure of surfaces to the active gas. This short exposure leads to a minimisation of absorption and hence a reduction in aeration and the shortest possible reliable cycle. Thus using this type of control sterilisation is achieved in the shortest possible time.

BRIEF DESCRIPTION OF THE DRAWING

The following is a description of a specific embodiment of the invention, reference being made to the accompanying diagrammatic illustration of an apparatus for sterilizing an enclosure.

DETAILED DESCRIPTION OF THE PREFERRED EMBODIMENTS

Figure 1:
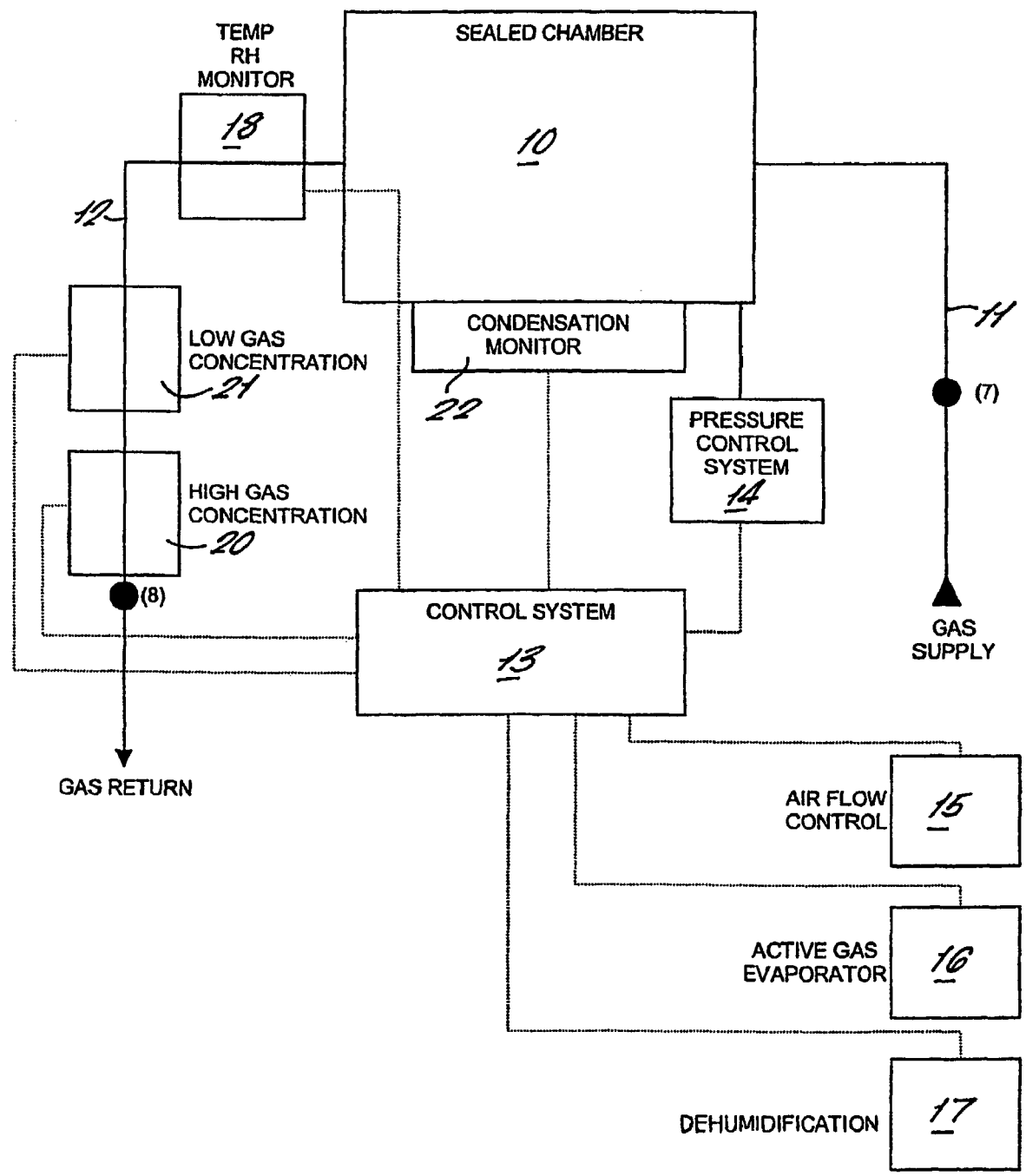

The apparatus for generating the sterilising gas is not critical to the control apparatus; the generating device must be capable of accurate control of the mass flow of gas to the chamber. It must also be able to control the humidity of the air delivered to the chamber during the dehumidification phase, and also that the concentration of active gas in the air stream must be variable according to the requirements of the control system.

It is further a requirement that a method is provided to deactivate the gas on leaving the chamber. A suitable gas generator is described in U.K. Patent Publication No. 2354443. A suitable method for controlling the gas concentration being delivered by the generator is described in our UK Patent Application No. 0006825.4.

A sealed chamber 10 is fluidly connected to a gas generator by pipes 11 and 12. The generator may be either a re-circulating type, or a flow through system or a combination of both types. The generator includes a control system 13 having a number of control functions. These include a pressure control system 14 for controlling pressure inside the sealed chamber, normally within the range of +200 Pa to −200 Pa. The system also includes a control 15 for the gas flow rate delivered to the chamber, together, a control 16 for the relative humidity and a control 17 active gas concentration. All of these functions are governed by the control system.

At the commencement of the sterilisation cycle the generator will pass air through the chamber 10 and temperature and RH monitors 18 measure the relative humidity. The output signal from the temperature and RH monitors will be used by the control system 13 to operate the dehumidification device 16 to achieve the required level of humidity at the sensor.

The apparatus described above is particularly suitable for use in the apparatus for sterilising an enclosure described and illustrated in our UK Patent Application No. 9922364.6.

Once the correct level of humidity has been achieved the controller will maintain this level by operation of the dehumidifier (19) for the required preset time interval.

At the end of the dehumidification hold time the controller will initiate the gassing phase of the cycle. During this phase the output of a high gas concentration sensor 20 is recorded to ensure that the correct levels of saturated vapour have been achieved. The high gas concentration sensor is located in series with a low gas centration sensor 21. Once saturation has been achieved inside the sealed chamber 10 condensation will start to form and be measured by the condensation monitor 22. The condensation monitor may be as disclosed in our UK Patent Application No. 0006822.1 which is an optical device or may be a device which determines electrical resistivity at a surface to detect condensation on the surface. When the required level of condensation has been achieved the control systems 13 will reduce or stop the flow of liquid to the gas evaporator in order to maintain the condensation for the required period of time. The dwell time for holding the condensation is temperature dependent, lowering the temperature reduces the efficacy of the sterilisation process and hence a longer dwell time is required. The time temperature relationship was defined by Swartling ⑥ and is programmed into the control system.

Once the end of the condensation dwell time has been reached the controller stops the liquid flow to the evaporator and delivers fresh clean air, which may be dehumidified to the sealed channel. This fresh clean air reduces the gas concentration inside the sealed chamber 10 and removes the surface condensation. The residual gas concentration leaving the chamber is monitored by the high and low concentration gas sensors 20 and 21. Once an acceptable level has been achieved the control system indicates that the cycle is complete.

REFERENCES

I. Dorothy M. Portner et al. Sporicidal effect of peracetic acid vapour. Applied Micro. Nov 1968 Vol 16 No 11 p1728–1785
II. Lack. A study of conventional formaldehyde fumigation methods. J. App. Bact 1990, 68, 000—000
III. Watling et al. The implications of the physical properties of mixtures of hydrogen peroxide and water on the sterilisation process. ISPE conference Zurich Sep. 1998.
IV. M-A Marcos et al. Pharmaceutical Technology Europe Vol 8 No 2 Feb. 99 (24–332)
V. Scratchard et al. J. Am. Chem. Soc., 74, 3715, 1952
VI. Swartling et al. The sterlising effect against *bacillus subtilis* of hydrogen peroxide at different temperatures and concentrations. J Dairy Res. (1968), 35, 423.

The invention claimed is:

1. A method of sterilizing a sealable enclosure comprising:
   initially adjusting the relative humidity in the enclosure to a required level,
   circulating a carrier gas to the enclosure at a temperature raised above ambient,
   supplying a sterilant vapor or vapors to the circulating carrier gas,
   distributing the gas/vapor throughout the enclosure,
   continuing to circulate the gas/vapor through the enclosure until sterilization has been completed,
   terminating the supply of sterilant vapor to the gas while continuing to circulate the saturated gas/vapor to maintain the condensate on the enclosure surfaces for a predetermined period of time, and
   extracting the sterilant vapor from the chamber; sufficient sterilant vapor or vapors being added to the carrier gas to saturate substantially the gas whereby, on cooling in the enclosure, a condensate of the sterilant vapor is formed throughout the enclosure, measuring the amount of condensate formed on the surfaces of the enclosure and continuing to circulate the gas/vapor until a required amount of condensate has been formed on the enclosure surfaces.

2. A method as claimed in claim 1, wherein the relative humidity of the enclosure is adjusted to about thirty to forty percent.

3. A method as claimed in claim 1, wherein the sterilant vapor or vapors comprise hydrogen peroxide vapor and water vapor.

4. A method as claimed in claim 1, wherein after said predetermined period of time for circulating the saturated gas/vapor, the gas/vapor is circulated over a catalyst to cause breakdown of the sterilant vapor into its constituent parts and water vapor is removed from the circulating gas, the dry gas being circulated through the enclosure until all of the sterilant has been extracted from the enclosure.

5. A method as claimed in claim 2, wherein the sterilant vapor or vapors comprise hydrogen peroxide vapor and water vapor.

6. A method as claimed in claim 3, wherein after said predetermined period of time for circulating the saturated gas/vapor, the gas/vapor is circulated over a catalyst to cause breakdown of the sterilant vapor into its constituent parts and water vapor is removed from the circulating gas, the dry gas being circulated through the enclosure until all of the sterilant has been extracted from the enclosure.

7. A method of sterilizing a sealable enclosure comprising:
   adjusting the relative humidity in the enclosure to a required level;
   circulating a carrier gas to the enclosure at a temperature raised above ambient;
   supplying one or more sterilant vapors to the circulating carrier gas sufficient to substantially saturate the gas;
   allowing the enclosure to cool until a condensate of the sterilant vapor is formed on surfaces throughout the enclosure;
   measuring the amount of condensate formed on the surfaces of the enclosure and continuing to circulate the gas/vapor through the enclosure until a required amount of condensate has been formed on the enclosure surfaces;
   reducing or terminating the supply of stenlant vapor to the gas while continuing to circulate the saturated gas/vapor to maintain the condensate on the enclosure surfaces for a predetermined period of time; and
   extracting the sterilant vapor from the chamber.

8. A method as claimed in claim 7, wherein the relative humidity of the enclosure is adjusted to about thirty to forty percent.

9. A method as claimed in claim 7, wherein the one or more sterilant vapors comprise hydrogen peroxide vapor and water vapor.

10. A method as claimed in claim 7, wherein after said predetermined period of time for circulating the saturated gas/vapor, the gas/vapor is circulated over a catalyst to cause breakdown of the one or more sterilant vapors into constituent parts and water vapor is removed from the circulating gas, the dry gas being circulated through the enclosure until all of the sterilant has been extracted from the enclosure.

11. A method as claimed in claim 8, wherein the one or more sterilant vapors comprise hydrogen peroxide vapor and water vapor.

12. A method as claimed in claim 9, wherein after said predetermined period of time for circulating the saturated gas/vapor, the gas/vapor is circulated over a catalyst to cause breakdown of the one or more sterilant vapors into constituent parts and water vapor is removed from the circulating gas, the dry gas being circulated through the enclosure until all of the stenlant has been extracted from the enclosure.

* * * * *

UNITED STATES PATENT AND TRADEMARK OFFICE
CERTIFICATE OF CORRECTION

PATENT NO. : 7,025,932 B2  
APPLICATION NO. : 10/221457  
DATED : April 11, 2006  
INVENTOR(S) : Martin et al.

Page 1 of 1

It is certified that error appears in the above-identified patent and that said Letters Patent is hereby corrected as shown below:

Title Page  
Item 57, Abstract, Line 10 of Abstract, after "has been formed on" remove "a"

Column 1  
Line 40, change "Chamber" to --chamber--  
Line 61, change "leave" to --leaves--  
Line 63, change "BI" to --B1--

Column 2  
Line 3, change "BI" to --B1--  
Line 63, change "Surface Sterilisation" to --surface sterilization--

Column 4  
Line 31, remove "also that"  
Line 48, change "16" to --17--  
Line 49, change "17" to --16--  
Line 57, change "16" to --17--  
Line 64, change "(19)" to --17--

Column 5  
Line 13, after "dependent" change "," to --;--  
Line 39, change "Scratchard" to --Scatchard--

Column 6  
Line 39, change "stenlant" to --sterilant--  
Line 65, change "stenlant" to --sterilant--

Signed and Sealed this

Seventh Day of November, 2006

JON W. DUDAS  
*Director of the United States Patent and Trademark Office*